United States Patent
Ganley et al.

(10) Patent No.: US 9,662,190 B2
(45) Date of Patent: May 30, 2017

(54) ADDRESSABLE MATRICES/CLUSTER BLANKS FOR DENTAL CAD/CAM SYSTEMS AND OPTIMIZATION THEREOF

(71) Applicant: Ivoclar Vivadent AG, Schaan (LI)

(72) Inventors: Robert A. Ganley, Williamsville, NY (US); Dmitri G. Brodkin, Livingston, NJ (US)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/018,064

(22) Filed: Sep. 4, 2013

(65) Prior Publication Data

US 2014/0010610 A1 Jan. 9, 2014

Related U.S. Application Data

(62) Division of application No. 12/118,981, filed on May 12, 2008, now Pat. No. 8,551,622.

(60) Provisional application No. 60/935,006, filed on Jul. 20, 2007, provisional application No. 61/024,935, filed on Jan. 31, 2008.

(51) Int. Cl.
  *G05B 19/4097* (2006.01)
  *A61C 13/08* (2006.01)
  *A61C 13/00* (2006.01)
  *A61C 5/77* (2017.01)

(52) U.S. Cl.
  CPC ............... *A61C 13/08* (2013.01); *A61C 5/77* (2017.02); *A61C 13/0022* (2013.01); *Y10T 409/30112* (2015.01); *Y10T 409/302968* (2015.01); *Y10T 409/305544* (2015.01); *Y10T 409/309016* (2015.01)

(58) Field of Classification Search
  CPC ............................. G06Q 10/043; A61C 13/08
  USPC ................................................... 700/171, 182
  See application file for complete search history.

(56) References Cited

U.S. PATENT DOCUMENTS

| 2,528,219 | A | | 10/1950 | Feagin |
| 5,383,752 | A | | 1/1995 | Rheinberger et al. |
| 5,691,909 | A | * | 11/1997 | Frey ................... G05B 19/4069 700/159 |
| 6,224,371 | B1 | | 5/2001 | De Luca |
| 6,231,799 | B1 | | 5/2001 | Kempf et al. |
| 6,454,568 | B1 | | 9/2002 | Beuschel et al. |

(Continued)

FOREIGN PATENT DOCUMENTS

| DE | 102008030050 | 8/2009 |
| JP | 2001054525 A | 2/2001 |

OTHER PUBLICATIONS

Rae et al., "Interpreting three-dimensional shape distributions" Proceedings of the Institution of Mechanical Engineers, Part C: Journal of Mechanical Engineering Science Jun. 1, 2005 vol. 219 No. 6, pp. 553-566.*

(Continued)

*Primary Examiner* — Mohammad Ali
*Assistant Examiner* — Emilio J Saavedra
(74) *Attorney, Agent, or Firm* — Ann M. Knab; Thad McMurray

(57) ABSTRACT

A cluster mill blank includes a framework constructed to cooperate with a blank holder of an existing CAD/CAM system, and a plurality of sub-blanks attached to the framework forming an addressable matrix or cluster blank. CAD/CAM systems including such a framework, as well as associated methods are described.

26 Claims, 13 Drawing Sheets

FIG.12

(56) References Cited

U.S. PATENT DOCUMENTS

| | | |
|---|---|---|
| 6,482,284 B1 | 11/2002 | Reidt et al. |
| 6,485,305 B1 | 11/2002 | Pfeiffer |
| 6,627,327 B2 | 9/2003 | Reidt et al. |
| 6,660,400 B1 | 12/2003 | Hintersehr |
| 6,669,875 B2 | 12/2003 | Meyertholen et al. |
| 6,769,912 B2 * | 8/2004 | Beuschel et al. ............. 433/163 |
| 6,775,581 B2 | 8/2004 | Landers et al. |
| 6,788,986 B1 | 9/2004 | Traber et al. |
| 6,905,293 B1 | 6/2005 | Filser et al. |
| 6,979,496 B2 | 12/2005 | Haymann et al. |
| 6,991,853 B2 | 1/2006 | Branco de Luca et al. |
| 7,024,272 B2 | 4/2006 | Thomas et al. |
| 7,110,849 B2 | 9/2006 | Landers et al. |
| 7,214,435 B2 | 5/2007 | Meyertholen et al. |
| 7,234,938 B2 | 6/2007 | Bodenmiller |
| 7,604,759 B2 | 10/2009 | Gubler et al. |
| 7,666,485 B2 | 2/2010 | Lal et al. |
| D618,807 S | 6/2010 | Konrad et al. |
| D627,472 S | 11/2010 | Wagner et al. |
| D627,473 S | 11/2010 | Wagner et al. |
| D627,889 S | 11/2010 | Wagner et al. |
| 8,021,154 B2 | 9/2011 | Holzner et al. |
| D675,325 S | 1/2013 | Ganley et al. |
| 2002/0137002 A1 | 9/2002 | Bodenmiller |
| 2003/0031984 A1 | 2/2003 | Rusin et al. |
| 2003/0132539 A1 | 7/2003 | Althoff et al. |
| 2006/0106485 A1 | 5/2006 | Landers et al. |
| 2006/0115794 A1 | 6/2006 | Sager |
| 2007/0048689 A1 * | 3/2007 | Holzner et al. ............... 433/229 |
| 2007/0136031 A1 | 6/2007 | Feldman et al. |
| 2007/0275352 A1 | 11/2007 | Gubler et al. |
| 2008/0241798 A1 | 10/2008 | Holzner et al. |
| 2009/0130634 A1 | 5/2009 | Ganley et al. |
| 2009/0274994 A1 | 11/2009 | Jung et al. |
| 2009/0275000 A1 | 11/2009 | Jung et al. |
| 2010/0028836 A1 | 2/2010 | Gubler et al. |
| 2011/0042880 A1 | 2/2011 | Konrad et al. |
| 2012/0214133 A1 | 8/2012 | Jung |

OTHER PUBLICATIONS

Qu et al., "A nesting algorithm for irregular parts and factors affecting trim losses" International Journal of Production Research vol. 25, Issue 3, 1987, pp. 381-397.*

* cited by examiner

ADDRESSABLE MATRICES/CLUSTER BLANKS FOR DENTAL CAD/CAM SYSTEMS AND OPTIMIZATION THEREOF

REFERENCE TO RELATED APPLICATIONS

This application is a divisional of U.S. application Ser. No. 12/118,981, filed May 12, 2008, which claims priority to U.S. Patent Application No. 60/935,006, filed Jul. 20, 2007 and U.S. Patent Application No. 61/024,935, filed Jan. 31, 2008, all of which are hereby incorporated by reference.

FIELD OF THE INVENTION

The present invention is directed to computer-aided systems for designing and manufacturing dental prostheses and restorations. The invention also relates to cluster mill blanks and their use in dental CAD/CAM systems to expand a range of systems compatible with a given blank; enable mill blank interchangeability with other systems; provide access to an increased variety of mill blanks for a given system; and maximize the system's versatility, selection of materials and efficiency of operation. According to certain aspects, the present invention is also directed to techniques and methods associated with the abovementioned cluster blanks.

BACKGROUND OF THE INVENTION

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Today, there is a progressively increasing trend in dentistry toward the use of automated technologies for treatment planning, virtual procedures, orthodontics, design and manufacturing of dental restorations both in dental offices (chair side) and dental laboratories (lab side). This trend, sometimes called "digital revolution," is most evident in lab side explosion of CAD/CAM technologies. A number of CAD/CAM systems available to dental laboratories has increased nearly ten-fold in the last decade. Currently, there are over 25 dental CAD/CAM systems and quite a few copy-milling systems using mill blanks in a variety of shapes and sizes. Blank shapes vary from simple geometries such as rectangular, cylindrical or hexagonal to more complex such as smart blanks described in U.S. Pat. No. 6,979, 496 which is incorporated by reference herein in its entirety. Their sizes range from about 0.5" to about 4" in length or diameter. Mill blanks are available in all 4 types of materials—metals, polymers (resins, plastics), ceramics and composites. Ceramic mill blanks can be divided into three major categories: feldspathic (leucite-based and sanidine or feldspar-based), glass-ceramic (lithium silicate, micaceous, etc.), and crystalline ceramic based such as alumina and/or zirconia (soft-sintered or fully dense). All three ceramic categories as well as composite blanks are already available or soon will be available in a variety of shades. Stocking the necessary inventory of shades for each given type of blank adds to economic pressures on the facility operating a CAD/CAM system.

A conventional 4 inch diameter disk-shaped zirconia blank 100 is illustrated in FIGS. 1-2. As illustrated therein a plurality of milled shapes 110 are formed in the zirconia blank 100. The blank 100 is formed entirely from zirconia, and therefore is quite costly. As illustrated in FIG. 2, use of such blanks 100 to form a plurality of milled shapes 110 results in a significant amount of wasted intervening block area 120 defined between the milling envelopes 112.

While CAD/CAM technology provides dental laboratories with opportunities for improved quality, reproducibility and elimination of human error, most CAD/CAM systems are geared to milling soft-sintered zirconia and thus lacking material selection to be competitive in a supersaturated and fast-paced market. Since the price for a CAD/CAM system, depending on manufacturer and configuration, runs from $50,000 to $500,000 only the largest labs and outsource centers can afford to operate multiple systems to expand their material selection. Most CAD/CAM systems manufacturers do not make their own blocks, rather they purchase them from suppliers such as Ivoclar, Vita or Metoxit, with an established core competency in dental or advanced materials development and manufacturing. Understandably, CAD/CAM materials are fairly expensive adding substantially to CAD/CAM system operating costs. For example, the price of ceramic milling blanks range from about $0.60 to $4.50 per gram of material. Yield per blank as defined in U.S. Pat. No. 6,979,496 is fairly low and most of it goes to waste.

The first CAD/CAM systems comprising milling units for chair side or lab side use such as Cerec (Sirona) and Lava (3M/ESPE) were closed systems wherein mill blanks are attached to a stub retainer, projection, mandrel, holder or carrier body, which have a unique patented geometry as described in U.S. Pat. Nos. 6,485,305 and 6,769,912 and can be also protected by a bar-code, thereby preventing interchangeability with other (CAD/CAM) systems. Variations of a work piece (millable part) on a stub assembly are also described in U.S. Pat. Nos. 7,214,435, 6,669,875, 6,627,327, 6,482,284, 6,224,371, 6,991,853 and 6,660,400. With advent of the open architecture systems, blank interchangeability between systems has become not only possible but extremely desirable. While the market is currently dominated by closed systems, the market penetration of open systems is steadily increasing. From 25 commercial CAD/CAM systems at least 5 or 6 are utilizing the same D-250 dental 3D scanner and DENTALDESIGNER™ dental CAD software (3Shape A/S, Copenhagen, Denmark). In an open architecture system, the blanks are not bar-code protected and any blank can be used as long as it fits the existing housing (blank holder, chuck, collect, support) of the milling unit.

Not all types of blanks can be economically produced in any shape and size. For example, zirconia and alumina blocks can be formed in any given shape and size to meet the demand for larger cases that can be milled from larger blanks. On the other hand, large feldspathic and glass-ceramic blanks are not so desirable due to a number of mechanical and economic constraints.

U.S. Patent Application 2006/0115794 appears to teach a system for continuous production of prosthodontic pieces such as crown cores, crowns or the like. The system utilizes turning and milling on a live center computer numerical control CNC machine of a zirconia rod stock that is automatically fed into the machine. Multiple pieces are cut one after another from the continuous rod stock. This patent application further appears to teach utilization of multiple machines wherein each machine is fed a rod stock of a different shape and/or size. A central control unit obtains specifications for a piece that is to be cut and selects the machine on which the piece is to be made by determining the rod stock that will require the least amount of cutting. In addition to the above mentioned economical and processing difficulties of fabricating and milling long rod stock from materials other than fully dense zirconia, considering the cost of the CNC machine, it is far more advantageous to enable one machine to mill all cases than to have many machines, each dedicated to a certain type of case.

U.S. Pat. No. 7,234,938 appears to disclose the multi-blank holder or workpiece receiver constructed as an elongated strip with multiples bores in it for embedding a plurality of identical blanks or workpieces. The invention relates to a milling/grinding machine, wherein, the workpiece receiver or mill blank holder has a plurality of bores arranged along its longitudinal axis, for receiving the workpieces or blanks. This invention also comprises a moldable embedding material disposed within the through-bore for retaining the workpiece within the through-bore. It further teaches a milling/grinding machine, comprising an embedding device for the automatic embedding of the workpiece in the workpiece receiver.

U.S. Patent Application 2006/0106485 describes the use of a virtual blank corresponding to a physical blank being processed to form a plurality of manufacturing features. This application further teaches virtual machining of each manufacturing feature of the plurality of manufacturing features into the virtual blank wherein each manufacturing feature exhibits an associative relationship with the coordinate system. Manufacturing instructions are generated to create the actual part by machining the plurality of manufacturing features into the blank. Such methods were pioneered in the automotive industry and described in U.S. Pat. Nos. 6,775,581; 7,024,272; 7,110,849 and U.S. Patent Application 2006/0106485, incorporated by reference herein in their entirety. It is also described in the white paper: Horizontal Modeling & Digital Process Design. The approach of electronically designing an article comprising an assembly of components is described in US Application 2007/0136031 incorporated by reference herein in its entirety. Again, this disclosure is not related to dentistry.

Thus, a need exists in the art for enabling blank interchangeability, maximizing yield per blank, and reducing material waste, to maximize the system's versatility, selection of materials and efficiency of operation. There is also a desire to reduce inventory of blanks thus reducing operating costs associated with commercial CAD/CAM systems.

SUMMARY OF THE INVENTION

The present invention provides techniques and arrangements that can optionally address one or more of the abovementioned shortcomings associated with the existing CAD/CAM systems. According to certain aspects, the present invention provides mill blanks by way of providing cluster blanks and software for efficient utilization thereof.

"Cluster blank" as used herein, is defined as a multiple blank assembly comprising at least two and preferably four or more individual blanks fixed to a framework (carrier body, housing, gripping yoke) compatible with the existing housing (blank holder, chuck, collect, support) of a milling unit, with minimal or no modification. The cluster blank thus forms a sort of addressable matrix of blanks that the milling unit or CAD/CAM system can access to efficiently mill shaped bodies into the blanks, with minimal waste and material removal, and with maximum interchangeability and flexibility. Accordingly, the terms "cluster blank" and "addressable matrix" may be used interchangeably herein.

Various cluster blanks can be formed from individual blanks using prefabricated or custom-made frameworks to enable use of said individual blanks in the maximum possible number of systems. A cluster blank can comprise the same individual blanks of identical size and shade, or different shades of the same size and type blank. Cluster blanks can also comprise various sizes and shades of the same blank type (material) and also a variety of different types of blanks from one or different manufacturers can be assembled on the same framework to make a "hybrid" cluster blank. To maximize the impact of cluster blanks on system efficiency, the present invention also provides for use of nesting software and system optimization software based on digital process design (DPD) methodologies using a virtual blank approach.

Accordingly, the present invention provides a cluster mill blank comprising a framework constructed to cooperate with a blank holder of an existing CAD/CAM system; and a plurality of sub-blanks attached to the framework.

According to further aspects the present invention provides a CAD/CAM system comprising a milling machine, a blank holder, a cluster milling blank comprising a framework constructed to cooperate with the blank holder, and a plurality of sub-blanks attached to the framework; and nesting software having at least a first order level of functionality.

According to yet another aspect, the present invention provides a method of milling objects using the CAD/CAM system described above, the method comprising analyzing historic actual milling data, or analyzing data corresponding to milled objects, with the nesting software thereby obtaining a size and shape distribution for milling envelopes and their correlation with specific types of dental articles, selecting a batch of cases corresponding to objects to be milled by selecting their corresponding electronic data, optimizing the number, type, size, arrangement, dimensions and/or shades of sub-blanks selected for milling the batch of cases, assembling the selected sub-blanks on to one or more frameworks utilizing one or more templates to produce one or more cluster blanks; and milling the objects into respective sub-blanks.

While the present invention is described herein mainly with reference to machining dental prostheses, it should be understood that the present invention is not so limited. For example, the principles of the present inventions can be applied to medical devices in general (e.g., implants, replacement joint parts, skeletal replacements, etc.) According to its broader aspects, the present invention can apply to the milling or shaping of essentially any three-dimensional object. Examples of three-dimensional objects include, but are not limited to, dental articles, such as, a coping, pontic, framework, denture teeth, space maintainer, tooth replacement appliance, orthodontic retainer, denture, post, facet, splint, cylinder, pin, connector, crown, partial crown, veneer, onlay, inlay, bridge, fixed partial denture, implant or abutment.

BRIEF DESCRIPTION OF THE DRAWING FIGURES

DETAILED DESCRIPTION OF THE INVENTION

Figure 1:
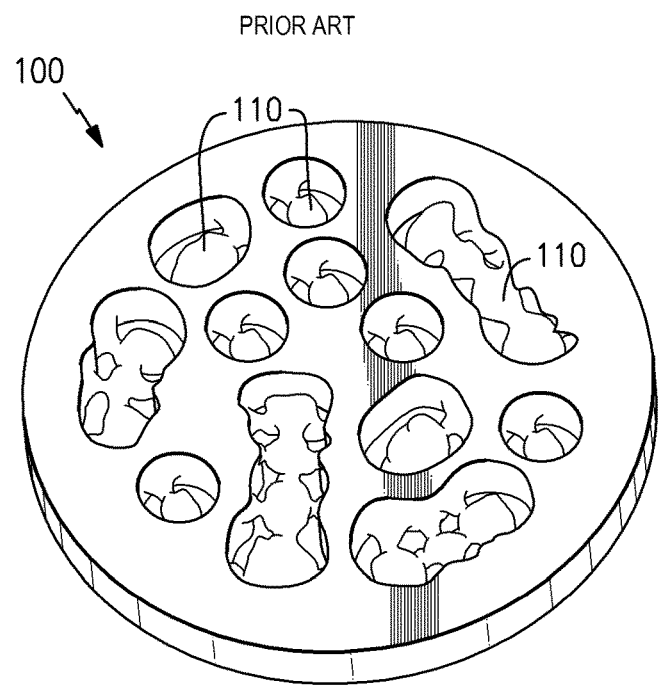
FIG. 1 is a conventional disk-shaped blank.

According to one optional aspect of the present invention, various cluster blanks are formed from individual blanks using prefabricated or custom-made frameworks to enable the use of individual blanks in the maximum possible number of systems. Hereafter individual blanks being assembled into a cluster blank will be termed sub-blanks. A cluster blank can comprise sub-blanks of identical size and shade, or different shades, sizes and/or types of sub-blanks. For example, a cluster blank can comprise various sizes and shades of the same sub-blank type and also a variety of different types of sub-blanks from one or different manufacturers can be assembled on the same framework to make a "hybrid" cluster blank. For example, E.MAX® CAD MO and/or LT blanks (Ivoclar) also known as "blue blocks" can potentially be processed by any robust CAD/CAM system utilizing wet-milling process and having software capable of designing full-contour restorations. An example of such a system capable of, but not yet milling "blue blocks" are ZENO®Tec system (Wieland), specifically ZENO®4820 and ZENO®3020 milling units interfaced with DENTALDESIGNER™ Software from 3Shape mentioned above. Examples of cluster blanks formed according to the present invention are shown in FIGS. 3-6.

Sub-blanks may be arranged in an addressable matrix, whereby the addressable matrix is designed from parameters received from a history of prior milling operations or prior business operations. The sub-blanks have properties associated with parameters received from a history of prior milling operations or prior business operations. These properties can include type of material, material characteristics, size of the sub-blank, shape of the sub-blank, and/or shade of the sub-blank. The parameters received from a history of prior milling operations can include type of case, material selection parameters, size of the dental article, shape of the dental article, shade of the dental article, optimal tool path, milling parameters, and statistics of milling envelopes used in the fabrication of dental articles. Examples of statistics of milling envelopes include shape and dimensions of the milling envelopes and the correlation of the milling envelopes with specific types of dental articles. Examples of milling parameters include type of tooling, depth of cut, feed rate, rotations per minute (rpm) and/or linear speed. Examples of type of tooling include a cutting, grinding or abrasive surface. The tooling can vary by material, shape, and/or size of tooling. Examples of cutting, grinding or abrasive surface include diamond, carbides, hardened steel, or ceramic. Examples of tooling shape include, but are not limited to cylindrical, conical, disc-shaped, ball-shaped, or fluted. The size of the tool may be dependent on diameter and length. Diamond tooling may include diamond grit. The depth of cut of the tooling may range in size from microns to millimeters. Further examples of milling parameters include post-milling parameters such as coating, glazing, or heat treatment parameters. Examples of parameters related to history of prior business operations include inventory used, inventory remaining, and case histories.

Figure 3:
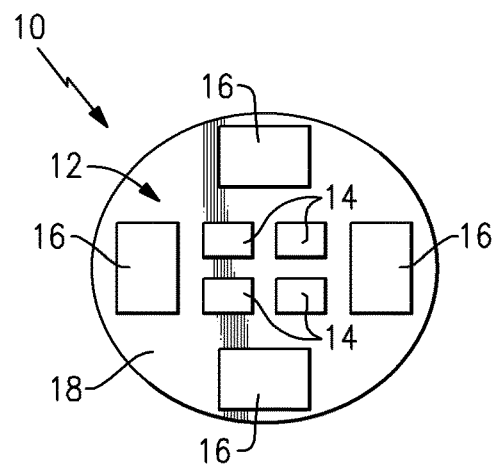
FIG. 3 is a cluster blank formed according to a first embodiment of the present invention.

A first cluster blank 10 formed according to certain embodiments of the present invention is illustrated in FIG. 3. As illustrated therein, the cluster blank 10 comprises a plurality of sub-blanks 12. According to the illustrated embodiment, two different types of sub-blanks 12 are included in the cluster blank 10. Namely, according to the illustrated embodiment, a plurality of first cluster blanks 14 are generally located in the central area of the cluster blank 10, and a second plurality of sub-blanks 16 are provided around the periphery of the cluster blank 10 according to a non-binding illustrative example, the first plurality of cluster blanks comprise C14 blue blocks and the second plurality of sub-blanks comprise B32 blue blocks. Each of the sub-blanks 12 are attached, or may be otherwise integrated with, a common 18. The framework 18 can be formed from any suitable material. For example, the framework 18 can be constructed from a metal such as steel or an aluminum alloy, a plastic or polymer such as PMMA, or composite material such as PARADIGM®MZ100 manufactured by 3M. The framework may comprise stationary or moving parts.

The cluster blanks 10, 20 as described in the illustrative embodiments above, may optionally be composed from a plurality of blue blocks and customized for use in the above-mentioned ZENO® Tec System.

Figure 4:
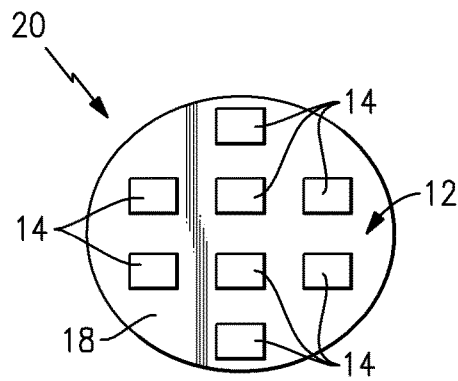
FIG. 4 is a cluster blank formed according to a second embodiment of the present invention.

A modification of the embodiment depicted in FIG. 3 is illustrated in FIG. 4. This embodiment is similar to the embodiment illustrated in FIG. 3, except for the arrangement and type of sub-blanks 12 associated with the framework 18. According to the embodiment illustrated in FIG. 4, the sub-blanks 14 each have the same construction, for example, each have the same size, shade, and/or are formed from the same material. According to one optional embodiment, each of the sub-blanks 14 are essentially identical to one another.

Frameworks can be in any shape or form including 2D and 3D. The frameworks can be mass-produced (pre-fabricated) or custom made for each desired pairing of system and mill blank. Sub-blanks can be mechanically attached (locked in) to a framework or alternatively adhesively bonded (glued) thereto or formed as an integral part of the framework. Sub-blanks can be also mounted into openings in the framework using castable mounting materials, modeling materials, polymer composites and other hardenable materials. Frameworks for cluster blanks can be designed for multiple uses, and/or as disposable implements. Furthermore, frameworks of cluster blanks can comprise a monolithic single part, or can comprise an assembly of a plurality parts or components. In the latter case parts or components of the framework assembly can be permanently affixed to each other or be detachable. The framework assembly can also comprise moving parts. For example, moving parts can be used to rotate or otherwise change the position of a sub-blank in a cluster blank before, during or after milling. This movement can be manual or automated and controlled by the same means as a CNC milling unit.

Figure 5:
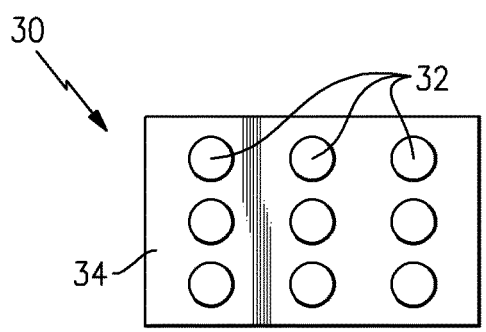
FIG. 5 is a cluster blank formed according to a further embodiment of the present invention.
Figure 6:
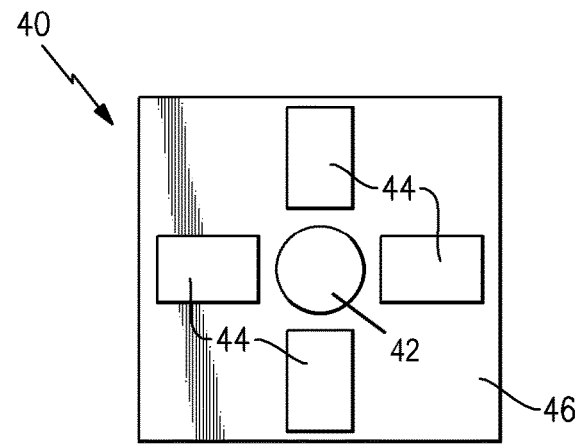
FIG. 6 is a cluster blank formed according to yet another embodiment of the present invention.
Figure 7:
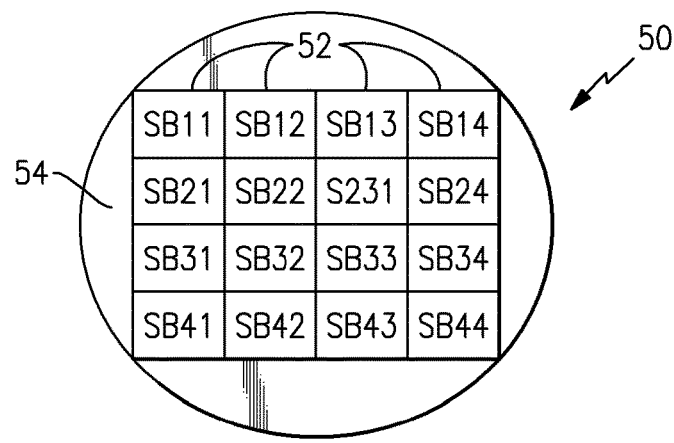
FIG. 7 is a cluster blank for according to yet an additional embodiment of the present invention.

Cluster blanks 30, 40 and 50 formed according to further embodiments of the present invention are illustrated in FIGS. 5-7, respectively.

As illustrated in FIG. 5, cluster blank 30 includes a plurality of sub-blanks 32 arranged on a polygonal framework 34. According to the non-limiting, illustrative embodiment, the sub-blanks comprise 9 round blocks arranged in three rows of three blocks each, and the framework 34 is substantially square. The block 32 and the framework 34 can be formed from any of the materials previously described herein.

As illustrated in FIG. 6, a cluster blank 40 formed according to an alternative embodiment of the present invention includes at least one sub-blank having a first characteristic and a plurality of second sub-blanks 44 having a second characteristic which differs from that of the at least one first sub-blank 42. According to the non-limiting, illustrative example, the first sub-blank 42 comprises a substantially round block, and the plurality of second sub-blanks 44 comprise polygonal or substantially square blanks symmetrically arranged around the first sub-blank 42. The first and second sub-blanks 42, 44 are attached to a polygonal framework 46. According to the non-limiting illustrative embodiment, the framework 46 is substantially square. Both the sub-blanks 42, 44 and the framework 46 can be formed from any of the previously described materials.

FIG. 7 illustrates a cluster blank 50 forming an addressable 4×4 matrix (SBij) comprising 16 sub-blanks 52 having various dental shades set in framework 54. According to one illustrative embodiment, if each sub-blank 52 represents one Vita Classic shade, this 4×4 addressable matrix can cover the entire Vita Classic shade range. In general each and all individual sub-blank positions in a given cluster blank/addressable matrix are assigned indices (numbers) based on specific ways and algorithms of how they are addressed by a software of a CAD/CAM system or operational software of a central processing facility such as nesting software types described below. For example, each sub-blank is assigned at least one number corresponding to its individual position/slot in a given cluster-blank in which the sub-blank is placed and at least the second number corresponding to the host cluster blank identification number or its place in a job queue, i.e. batch of cases to be milled. In this case cluster blank/addressable matrix of FIG. 7 is represented by a vector $SB_{km}$, where k corresponds to a place of a cluster blank in a job queue and m varies from 1 to 16 for the total number of 16 sub blank positions in a given cluster blank. Operating software adds other vectors to the addressable matrix such as the ones associated with specific sub-blank material, size, shape, shade and also milling parameters and case specifics. Therefore, each physical cluster blank/addressable matrix is represented by in at least the same size or larger "virtual" matrix in CPU and operating memory of a CAD/CAM system. The CAD/CAM system or milling center addresses the addressable matrix via its operational software or other means to automate the operations, saving time and money and minimizing waste. Thus the required optimization can be conducted by well known methods used in operations research and image processing such as factor analysis based on eigenvectors and eigenvalues.

As nearly all dental CAD/CAM systems are capable of milling plastic (e.g. PMMA) or composite material, frameworks formed from such materials can be milled, modified or optimized using the same milling unit and nesting software used to mill the blanks. Furthermore, the frameworks can be re-used, making their fabrication in the same milling unit even more economical. Compared to attachment onto a stub or mandrel, like in the Sirona system, attachment along the entire perimeter of a blank lowers stresses during milling and thus lowers strength and stiffness requirements for the framework material, thus making PMMA or polymer composite materials a feasible choice for cluster blank frameworks.

Furthermore open architecture systems are not limited to CNC milling machines specifically designed for dental use, practically any robust 3-axis or higher CNC machine can be utilized. More and more off-the-shelf CNC machines are being modified for dental use, i.e. fitted with a blank holder and interfaced with an open architecture scanner such as 3Shape's D-250, and used in large labs and milling centers for commercial production of dental articles primarily such as zirconia frameworks and custom implant abutments. For a custom made system the cluster blank approach is most advantageous in that it allows one to "many" the existing range of blocks to a given milling unit without serious modification of the machine hardware.

According to another aspect, the present invention provides for nesting software to be used in conjunction with cluster blanks. Nesting software can convert physical m-unit addressable matrix (comprising m sub blanks) into a multidimensional matrix by adding dimensions related to the type and other characteristics of sub-blanks, assignment of milling subroutines and/or algorithms optimizing tool path, tool selection, depth of cut, feed rate, RPM, linear speed and other milling parameters. One of the added dimensions for computer representation of an addressable matrix can be assembly instructions if the addressable matrix is assembled automatically. If necessary, sub-blanks and/or frameworks of cluster blanks are marked with indices or alphanumeric codes, barcodes, or other form of identification in any computer-readable format. Alternatively, frameworks of cluster blanks comprise magnetic strips, microelectronic chips or other re-writable data storage microdevices that carry identification and any other information relevant to milling and processing of a given cluster blank. This is especially useful when the CAD/CAM system is not equipped with nesting software.

An example of nesting software of the first order (as defined below) is given in U.S. Pat. No. 5,662,566, incorporated by reference herein in its entirety. Currently, nesting software is hardly being utilized in dental CAD/CAM systems and its use is limited to mapping parts to be milled into individual large-size blanks (mill jobs) to maximize an average yield per blank, wherein the average yield per blank is calculated as the weight of a finished restoration divided by a weight of a blank prior to being shaped by material removal. Cluster blanks of the invention allow for a much broader use of nesting software in conjunction with actual cluster blanks, and in certain embodiments nesting software also enables the use of virtual blanks.

Figure 2:
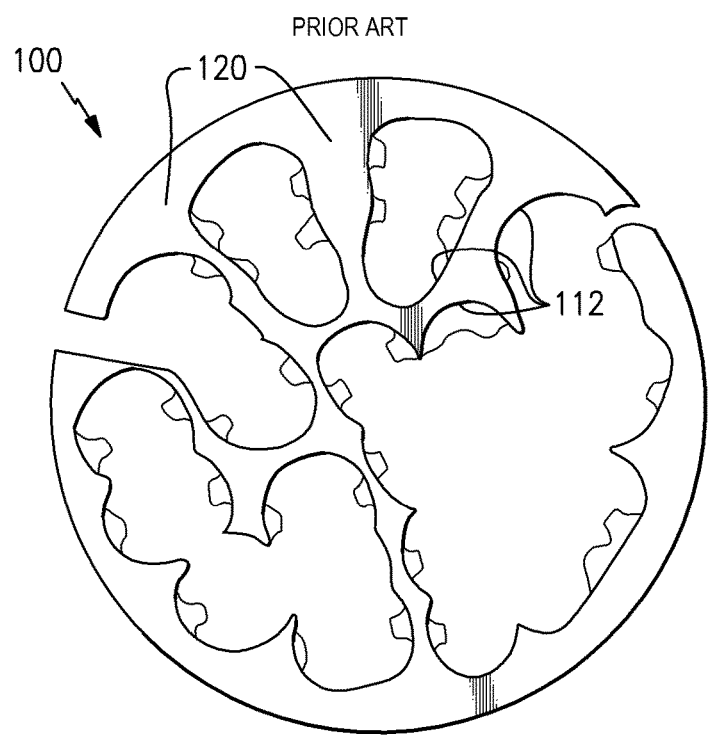
FIG. 2 is illustrative of the waste from milling the blank of FIG. 1.
Figure 8A:
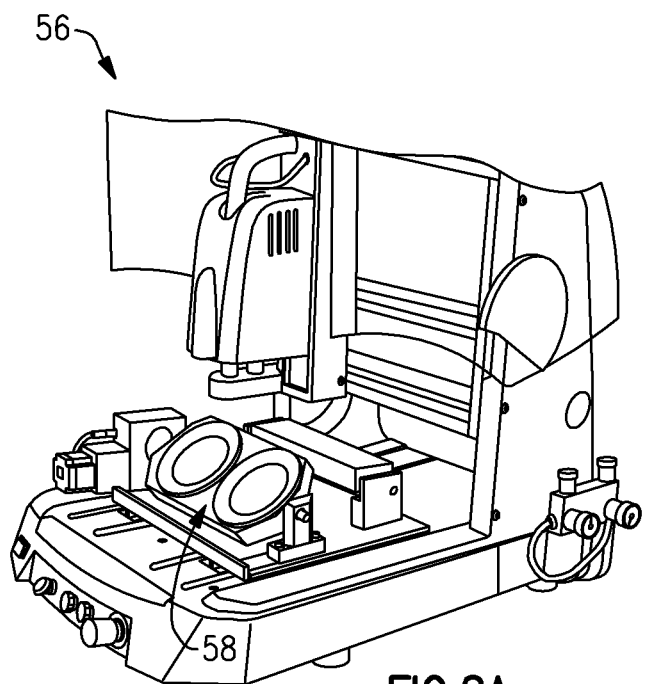
FIG. 8a illustrates a conventional CAD/CAM milling machine comprising a two disk milling blank holder in open position.

Nesting software is becoming a necessity for systems capable of milling large blanks. It is more imperative for milling cluster blanks. To illustrate the embodiments of this invention related to applications of nesting software in conjunction with cluster blanks, a 4" diameter disk-shaped blank as a typical example of a large single blank can be beneficially converted into a cluster blank. Hereafter the former is called a precursor blank and the latter is referred to as an equivalent cluster blank. These blanks made of soft-sintered zirconia can accommodate up to 10-15 mill jobs or 20-40 units varying from single units up to a 14-unit round house (see FIG. 8A). FIGS. 1-2 are illustrative of how such a blank looks after milling wherein the arrangement of mill jobs were not optimized leading to the actual yield of much less than 50% of the blank material. The holes left after milling individual cases define milling envelopes for these cases. The term milling envelope is used to explain various aspects of the present invention related to use of nesting software. A milling envelope is defined by its maximum length (MEL) and maximum width (MEW) provided that its depth is equal to the thickness of the blank.

It is important to note that although 4" round zirconia blanks are used in the illustrative examples of large blanks (precursor blanks) converted into equivalent cluster blanks, zirconia is not the only dental material that can be produced in a plurality of small and large shapes millable into single or multi-unit frameworks according to the present invention. For example, lithium silicate-based glass ceramics, which can be easily processed by machining into dental articles without undue wear of the milling tools and which subsequently can be converted into lithium disilicate restorations showing high strength of up to about 800 MPa are useful for single units as well as multi-unit dental restorations. Glass ceramics are shaped while in the glass state thus any glass-forming, glass-shaping technique can be potentially used for these materials. Other examples of strong dental materials formable into any shape and form, and further amenable for milling into multi-unit dental articles are dental alloys. Zirconia, glass-ceramics and alloys can be produced as simple shapes (rectangular, cylindrical, disk or polygon) or complex shapes ("smart" or near-net shapes) of any size. The driving force of reducing waste is equally strong for all these materials. If nesting software were to be used, the material waste would be much less than that shown in FIGS. 1-2. Alternatively sub-blanks can be assembled into a cluster blank, which will further reduce the waste perhaps even ten-fold compared to application of the first order nesting software to one or few large blanks. The further reduction of waste achieved according to the present invention comes from synergetic use of cluster blanks in combination with higher order nesting software, as described in the embodiments below.

The nesting software estimates the size and shape of milling envelopes corresponding to mill jobs in a job queue based on prior statistics or case electronic data, computes the required number of sub-blanks and frameworks, orders assembly of the sub-blanks and frameworks into the required number of cluster blanks, and optimally distributes mill jobs between the sub-blanks and the cluster blanks to minimize material waste and shade inventory.

In relation to the present invention, existing and future nesting software modules can be classified based on the level of intelligence and number of cases they can handle concurrently, i.e., using an "N/n" ratio wherein "N" is the number of cases "optimized" concurrently (Characteristic Batch Size) and "n" is the average number of individual units per blank. The function of nesting software is to maximize an average yield per blank and therefore to optimize "n" (not necessarily maximize), i.e. to optimize (and not necessarily minimize) number of blanks used for milling the characteristic number of cases, "N", relevant to operations of the given CAD/CAM facility. In terms of its use in the embodiments of the present invention, nesting software is classified as first, second and the third order based on its ability to simultaneously handle smaller or larger batches (queue) of cases, i.e., the N/n ratio. Examples of "n" are 7 or greater, 10 or greater and 30 or greater.

Figure 8B:
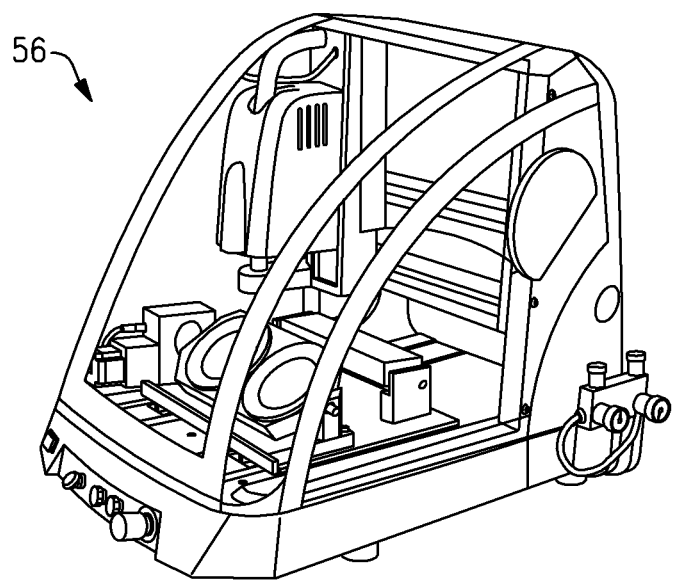
FIG. 8b illustrates a conventional CAD/CAM milling machine comprising a two disk milling blank holder in closed position.

The first order nesting software, wherein N/n<10 is capable of maximizing yield from a given blank, i.e. it can position consecutive mill jobs within the blank being milled to minimize waste. The related procedure amounts to distributing mill jobs accumulated in a queue allocated for one or a set of new blank(s) installed in a fixture or a cartridge of the milling unit. In other words the first order nesting software fits a limited number of individual cases into a volume of a blank. As the queue of mill jobs is small and different each time, the result is also different each time and no patterns can be elucidated. That is about where the industry is now. Currently, the holders capable of housing large multi-case blanks are limited to carrying a maximum of two blanks at a time (for example, see FIG. 8). For example, N/n is 0.55 and 0.35 for blanks of FIGS. 1 and 2, respectively. If both blanks were milled in a system using nesting software in combination with a milling unit equipped with a two-blank holder the resulting average number of units per blank would be 26.5 and the associated N/n ratio would be 0.87 (see Table 1 below). From the analysis of the data in a Table 1, it was concluded that about 30 is a good estimate of the "optimized" average number of milled units per 4" round blank.

TABLE 1

Examples of N/n calculation

| Blank | Number of cases, N | Number (or average number) of units per blank, n | N/n |
|---|---|---|---|
| first 4" disk | 12 | 22 | 0.55 |
| second 4" disk | 11 | 31 | 0.35 |
| Combination | 23 | 26.5 | 0.87 |

The first order nesting software is used for directing mill jobs into known positions within a cluster blank where the corresponding sub-blanks are located, i.e. correctly positioning milling envelopes corresponding to each mill job within the appropriate sub-blanks of a cluster blank. This function will be referred to as placement function. Waste is thus limited to two components: 1) material removed during milling of a sub-blank; and 2) material thrown out, i.e. volume difference between the actual milling envelope and the corresponding sub-blank of a cluster blank. Most of the waste is now avoided by the use of a framework or template of the cluster blank. The second component of waste is subject to minimization through use of higher order nesting software as shown below.

The second order nesting software, wherein N/n=10-100, is capable of maximizing yield from a relatively large batch of blanks, wherein the size of the batch N, is operations-relevant, i.e., related to a characteristic time sufficient to acquire statistically significant data depending on the size and logistics of a given CAD/CAM facility. Hereinafter N is called Characteristic Batch Size if it is operations-relevant, namely if it is defined by the logistics of operations of a given milling center and market requirements. For example, under steady state operations each business day the number of cases received (daily input) is equal to the number of cases shipped to the customers (daily output). An average residence time of a case in a milling center, or time passed from a case entering milling center to a case leaving it, is limited by the market situation. Currently, for a milling center to be successful the turn-around time should be less than a week, i.e., customers should receive their cases back in less than a week, therefore the residence time of the case in a milling center should be 3-5 business days, regardless of the complexity of the case. Therefore, each day the number of cases in the pipeline of a given milling center is 3-5 times the daily input/output. Therefore Characteristic Batch Size is at least equal to the number of cases in a daily job queue for a high productivity CNC milling machine and can be as large or larger than total daily case load, i.e., all the cases, in all stages, in the pipeline of a given milling center or the daily job queue for the whole milling center. Examples of high productivity CNC milling machines especially suited for large milling centers are ZENO® 6400 L milling machine with four material holders and Etkon's HSC (High Speed Cutting) machines.

Small to mid-size milling centers process from 100 to 500 cases a day or 500-3000 cases a week. If only 4" round blanks are used in such a milling center, assuming an "optimized" n value of 30, the resulting N/n ratio is in the range of 17-100. The nesting software of the second order is not just fitting a limited number of individual cases in a volume of a large blank as does the first order nesting software. Second order nesting software also optimizes the arrangement and assortment of sub-blanks assembled into a range of cluster blank templates for a given master type, thus minimizing waste and shade inventory for much larger batches of cases.

Figure 9:
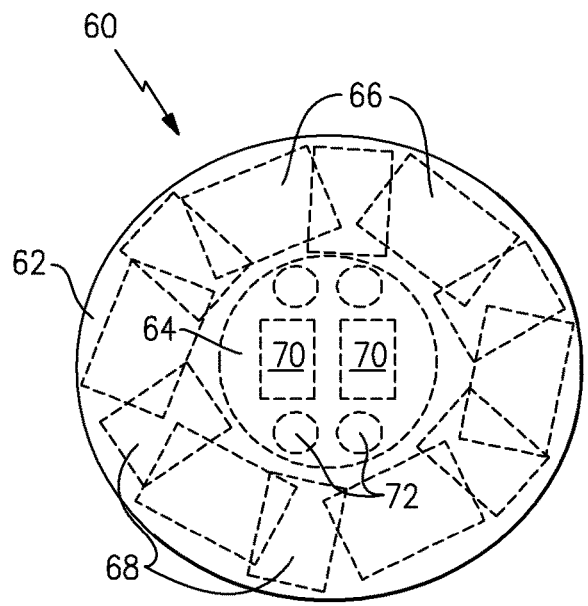
FIG. 9 is a schematic illustration of a cluster blank master template formed according to the principles of the present invention.
Figure 10:
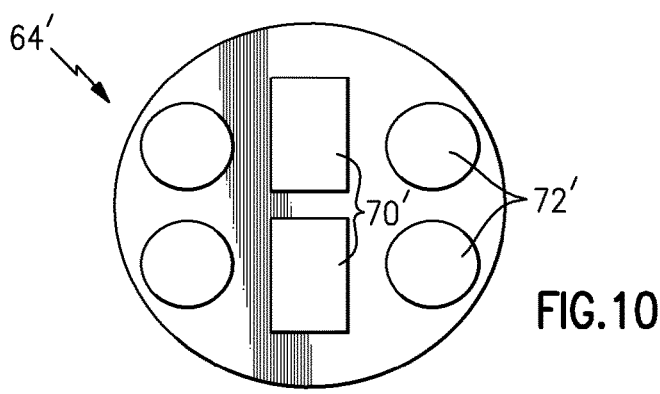
FIG. 10 is a modification of the master template of FIG. 9, constructed according to one embodiment of the present invention.
Figure 11:
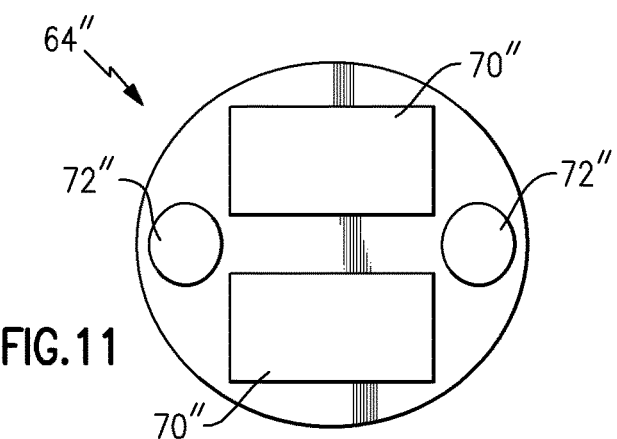
FIG. 11 is a modification of the master template of FIG. 9, constructed according to another embodiment of the present invention.

A possible master template 60 master type framework or simply master for a cluster blank equivalent to a 4" round precursor blank is shown in FIG. 9. The template 60 for this master type comprises an outer ring 62 and an inner core 64 wherein outer ring 62 can hold larger size sub-blanks such as either 66 or 68, and inner core holds smaller size sub-blanks 70, 72. While the overall dimensions of these templates are the same and specific to a given master type, there may be a difference in a number and size of openings (as represented in the illustrative embodiment in broken lines) in each template. For example, the template shown in FIG. 9 can house the largest sub-blanks 66 for 4 to 6-unit frameworks in the outer ring according to one configuration, or medium sub-blanks 68 for 2 to 3-unit frameworks in the outer ring according to an alternative configuration. The inner core can likewise have different arrangements of relatively smaller sub-blanks. For example, as illustrated in FIG. 10, the inner core 64' may comprise an arrangement of first polygonal sub-blanks 70' and second round or oval sub-blank 72'. According to the illustrated example, the inner core 64' comprises an arrangement of 2 relatively large polygonal blanks 70' and four relatively smaller round or oval blanks 72'. A further alternatively constructed inner core 64" is illustrated in FIG. 11. As illustrated therein, the inner core 64" arrangement may comprise an arrangement of first polygonal sub-blanks 70" and second round or oval sub-blanks 72". According to the illustrated example, the inner core 64" comprises an arrangement of 2 relatively large polygonal blanks 70" and two relatively smaller round or oval blanks 72". Any type of arrangement of sub-blanks may be used, such as for example, large sub-blanks for the manufacture of two- to three-unit articles and small sub-blanks for the manufacture of single-unit dental articles.

The maximum number of sub-blanks depends on the construction and diameter of the template, and also on the arrangement, shape and size of the constituent sub-blanks. Based on feed-back from the nesting software of the second order, some and not necessarily all the available positions on the template are filled, or are necessarily filled with sub-blanks of the same shade.

Figure 12:
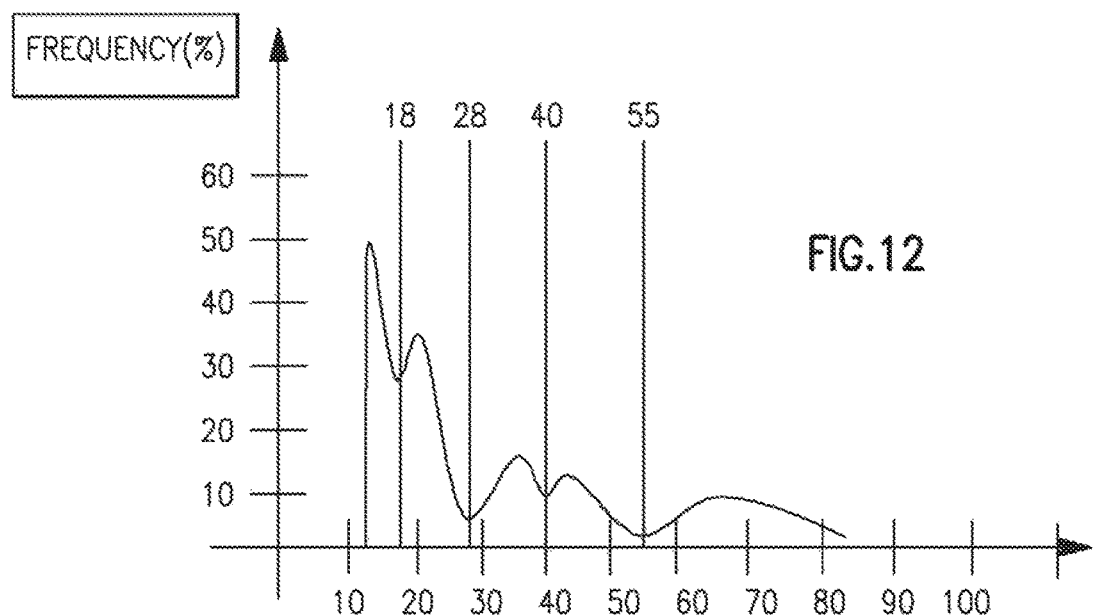
FIG. 12 is a graphical representation of the size distribution of milling envelopes.

In one aspect of the invention, the method is provided wherein a CAD/CAM system equipped with nesting software collects data to determine the types of sub-blanks that will be required for future operations. At the beginning of the process, for a sufficient time period, the 4" round zirconia precursor blanks are milled rather than the cluster blanks and the nesting software operates as $1^{st}$ order simultaneously collecting statistics on the size distribution of milling envelopes. Based on actual milling of precursor blanks, the size distribution diagrams, histograms, curves or surfaces are generated for milling envelopes corresponding to posterior and anterior single dental units and multi-unit dental frameworks. FIG. 12 shows 2D "Frequency vs. MEL" section of one such curve wherein milling envelopes are characterized in the most simplistic way by their maximum length (MEL) and maximum width (MEW). Even in this simple representation the resulting size distribution is a complex surface in an orthogonal 3D system of coordinates also shown schematically in FIG. 12. The size distribution curve exhibits peaks and valleys the physical meaning of which is shown in the Table 2 below.

TABLE 2

Positions and physical meaning of peaks and valleys on milling envelope size distribution curve

| Positions of peaks and valleys on milling envelope size distribution curve | Peak* MEL, mm | Corresponding MEW, mm | Valley** MEL, mm | Corresponding MEW, mm |
|---|---|---|---|---|
| $1^{st}$ (Anterior single units) | 15 | 13 | 18 | 15 |
| $2^{nd}$ (Posterior single units) | 22 | 16 | 28 | 19 |
| $3^{rd}$ (3-unit frameworks) | 35 | 21 | 40 | 22 |
| $4^{th}$ (4-unit frameworks) | 45 | 23 | 55 | 23 |

*The most frequent value of MEL for certain type of cases, e.g. the most frequent milling envelope length (MEL) for a three unit bridge framework is about 35 mm.

**In-between values correspond to rarely occurring, the largest n-unit cases and rarely occurring, the smallest (n+1)-unit cases. For example the holes (milling envelopes) left after milling of nearly all 3-unit frameworks are shorter than 40 mm, however the holes for 4-unit frameworks are mostly longer than 40 mm. Therefore the 40 mm×22 mm sub-blank will fit most of 3-unit frameworks.

The milling envelope size distribution presented in FIG. 12 leads to logical selection of cylindrical sub-blanks of about 15-18 mm in diameter or rectangular sub-blanks of 15×18 $mm^2$ in cross-section for anterior single units, 19×28 $mm^2$ sub-blanks for posterior single units, 22×40 $mm^2$ sub-blanks for 3-unit frameworks, and 23×55 $mm^2$ sub-blank for 4-unit frameworks. With more accurate statistics corresponding to a larger volume of cases these dimensions could be further refined into subcategories related to anterior and posterior multi-unit frameworks. These sub-blanks are also required in at least two different thicknesses, therefore to minimize zirconia waste, specifically the second component of waste, the nesting software should manipulate with at least 8 different sub-blank sizes arranging them in outer ring/inner core templates shown, for example, in FIG. 9.

Statistical analysis of size and shape distribution for milling envelopes yields the optimal sub-blank dimensions. It is found that if 1) the variety of sub-blank shapes and sizes is consistent with the number of characteristic features (e.g. MEL and MEW peaks or valleys) of the milling envelope size distribution curves; and 2) the number of available modifications of the utilized master template allows for the arrangement of these characteristic shapes and sizes to match the given operations—relevant batch of cases in the most optimal way, it will lead to reduction of the second component of waste and also to reduction of shade inventory. The optimal number of shapes and sizes for sub-blanks can be elucidated logically by analysis of data provided by the nesting software of the second order. The nesting software of the second order is also capable of recommending on its own the minimum number of sub-blank sizes to achieve the required minimization of waste and shade inventory. However it is not capable of designing or re-designing a master template and developing the required number of its modifications. The latter task will require nesting software of the third order which can also use a virtual blank approach in lieu of actual statistics acquired during milling.

The third and highest order nesting software, N/n>100 can be deployed in the large central processing facilities and milling centers processing more than a thousand cases a day. The potential economy of scale in such facilities justifies the customized sub-blanks variety and custom cluster blank designs. The designs should be changed periodically to respond to changing demands of the market. These facilities are large enough to dictate their parameters to the manufacturers of sub-blanks, CAD/CAM units and/or software. The nesting software appropriate for such facilities has design capabilities integrated into a process feed-back loop that allows for modification of the range of sizes and shapes for constituent sub-blanks and the corresponding template design based on the actual feed-back data. For example nesting software of the third order is capable of modifying template dimensions, number, size, shape and arrangement of sub-blanks in a template, as well as to select the optimal shade distribution if the cluster blank template and cluster blank housing/holder dimensions were designed parametrically within the design envelope given by CNC machine support dimensions.

Since prior to milling, all mill jobs exist as CAD files, STL files or any other standard digital representations of complex 3D objects, the optimization functions described above can be implemented prior to actual milling or concurrently with milling. For example the size and shape distribution for milling envelopes can be forecasted, i.e., derived or extrapolated from the plurality of the CAD files to be milled. This data can be further used to assemble, design and fabricate sub-blanks and templates/frameworks for cluster blanks. This and other capabilities and functions of different order nesting software are compared in a table below.

TABLE 3

Nesting Software Capabilities and Functions

| Nesting Software Capabilities/Functions | $1^{st}$ Order Nesting Software | $2^{nd}$ Order Nesting Software | $3^{rd}$ Order Nesting Software |
|---|---|---|---|
| Characteristic N/n ratio: where "N" - number of cases "optimized" concurrently and "n" - average number of individual units per blank. | <10 | 10-100 | >100 |
| Ranges for Characteristic Batch Size, N, for n = 7 corresponding to the optimized average number of units milled from a cluster blank (e.g., FIGS. 25-27) | <70 | 70-700 | >700 |
| Ranges for Characteristic Batch Size, N, for n = 30 corresponding to the optimized average number of units milled from a cluster blank | <300 | 300-3000 | >3000 |
| Single blank optimization function: minimizes waste/maximize yield from a single large blank | X | X | X |
| Placement function: positions mill jobs onto sub-blanks of equivalent cluster blank | X | X | X |

TABLE 3-continued

Nesting Software Capabilities and Functions

| Nesting Software Capabilities/Functions | 1st Order Nesting Software | 2nd Order Nesting Software | 3rd Order Nesting Software |
|---|---|---|---|
| Statistical function: gives actual statistics on size and shape distribution for milling envelopes | | X | X |
| Sub-blank optimization function: yields the optimal sub-blank dimensions and optimal number of sub-blanks | | X | X |
| Planning function: optimizes arrangement and assortment of sub-blanks to be assembled into a range of cluster blank templates to minimize waste and shade inventory for a large batch of cases | | X | X |
| Virtual statistics: uses CAD files for future mill jobs to forecast size and shape distribution for milling envelopes | | | X |
| Cluster blank template optimization function: yields the optimal template design and optimal number of master template modifications | | | X |
| Robotic function: automated template fabrication and assembly of cluster blanks optionally based on virtual blank method | | | X |

According to nesting software functions summarized in the table above, there is provided a method of employing nesting software for effective utilization, design and assembly of cluster blanks to optimize placement of sub-blanks in a cluster blank assembly, minimize waste and inventory of shades. The method can optionally comprise system optimization software based on digital process design (DPD) methodologies, specifically horizontally structured CAD/CAM manufacturing using a virtual blank approach. Said method comprises one or more of the following operations in any combination and in any order:

1) Analyze historic milling data provided by nesting software related to placement of units on precursor blanks to gain size and shape distribution for milling envelopes.

2) Select an operations-relevant batch of cases to be milled represented by their corresponding CAD, STL or equivalent files and a range (of designs) of cluster blank templates to be fitted with an optimal arrangement of sub-blanks.

3) Alternatively to 1) use higher order nesting software to provide "virtual statistics" extrapolating milling envelope size and shape distribution from CAD files or any equivalent digital representations of cases to be milled.

4) Based on actual or virtual statistical analysis of the operations-relevant plurality of milling envelopes establish the optimal number of sub-blanks, their shapes and dimensions.

5) Assemble the selected sub-blanks in the selected templates to produce cluster blanks and mill the cases as directed by nesting software.

6) Re-acquire actual or virtual statistics on milling envelopes and yields.

7) Modify or redesign templates based on maximum average yield, minimum waste per sub-blank and minimum sub-blank shade inventory criteria.

8) Mill modified or redesigned templates from plastic precursor blanks using the same CAD/CAM system.

9) Alternatively, mass production of templates can be carried out using specialized equipment or can be outsourced.

10) Assemble cluster blanks for milling the next operations-relevant batch of cases as directed by nesting software.

11) Alternatively, at least some of operations 5) through 10) can be automated by the nesting software of the third order and carried out robotically.

It should be noted that if the operations 5) through 10) are automated by the nesting software of the third order, it is de facto functioning as the manufacturing platform, specifically a digital manufacturing platform. Currently, perhaps there is an advantage to a milling center in operating CAD/CAM systems of different types but with increasing demand for standardization and raising market penetration of open architecture systems the driving force to operate a one type, one platform system capable of milling all types of materials will increase progressively. The need in such a manufacturing platform for large central processing facilities and milling centers will increase greatly with further progress of digital revolution in dentistry, advent of impression-less dentistry and web-based processing centers.

Figure 13:
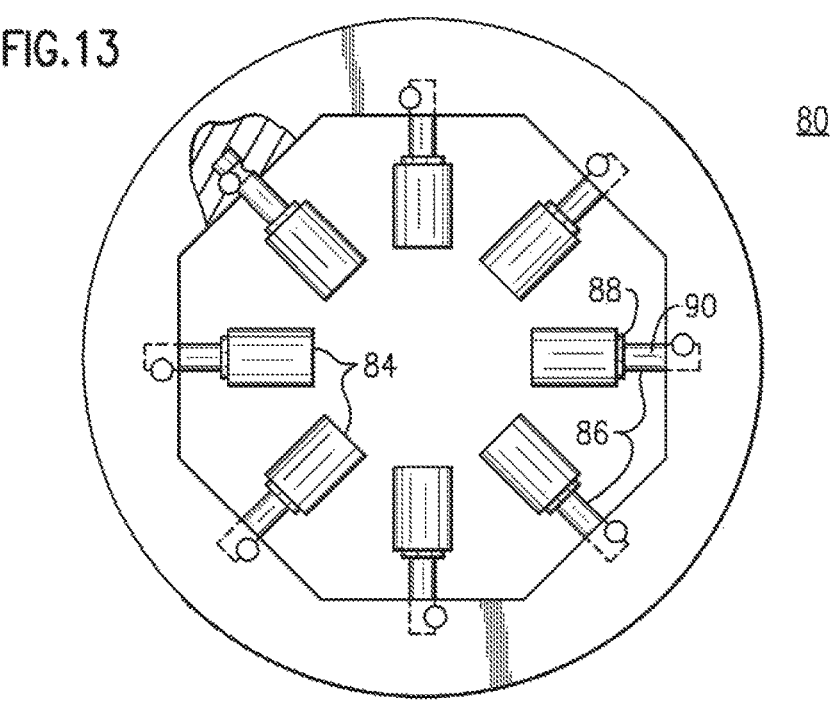
FIG. 13 is a top perspective view of sub-blanks mounted onto a framework in accordance with an embodiment of the present invention.
Figure 14:
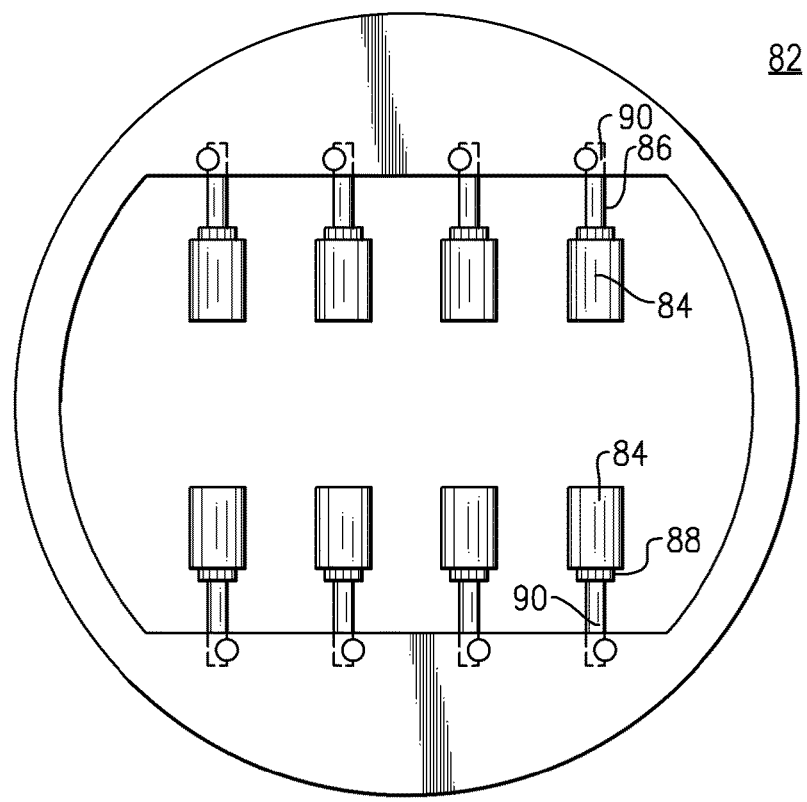
FIG. 14 is a top perspective view of sub-blanks mounted onto a framework in accordance with an embodiment of the present invention.

FIGS. 13 through 24 illustrate sub-blanks mounted in frameworks by various means of attachment. FIGS. 13 and 14 illustrate different embodiments of the invention having round frameworks 80 and 82. Framework 80 is a round configuration having sub-blanks disposed along the periphery of framework 80. Framework 82 has a set of sub-blanks disposed in two rows at opposite sides of the framework. Each sub-blank 84 is attached to a support 86 having a flange 88 attached to shaft 90 having a longitudinal axis that is attached to framework 80. Sub-blank 84 may be glued or otherwise adhered to flange 88. Shaft 90 may have any cross-sectional shape such as hexagonal or octagonal, although it is preferable that it has a round cross-section. Shaft 90 may be snapped into frameworks 80 and 82. Alternatively, shaft 90 may contain a groove that extends about its circumference to receive a set screw or other structure.

Figure 15:
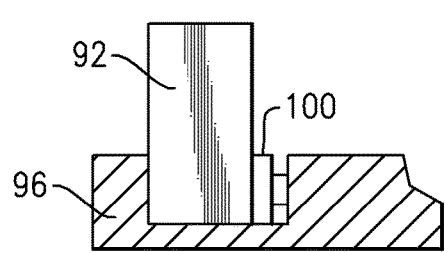
FIG. 15 is a fragmentary perspective view of a sub-blank mounted in a framework in accordance with an embodiment of the present invention.
Figure 16:
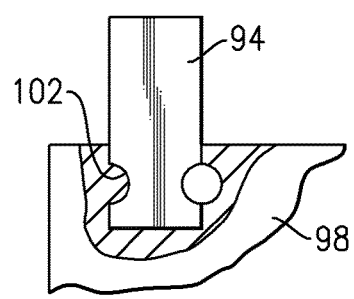
FIG. 16 is fragmentary perspective view of a sub-blank mounted in a framework in accordance with an embodiment of the present invention.

FIGS. 15 and 16 show sub-blanks 92 and 94, respectively attached to a framework 96 and 98, respectively. In FIG. 15, sub-blank 92 is nested in framework 96 by support 100. FIG. 16 shows sub-blank 94 having a notch 102 thereon for attachment to framework 98.

Figure 17:
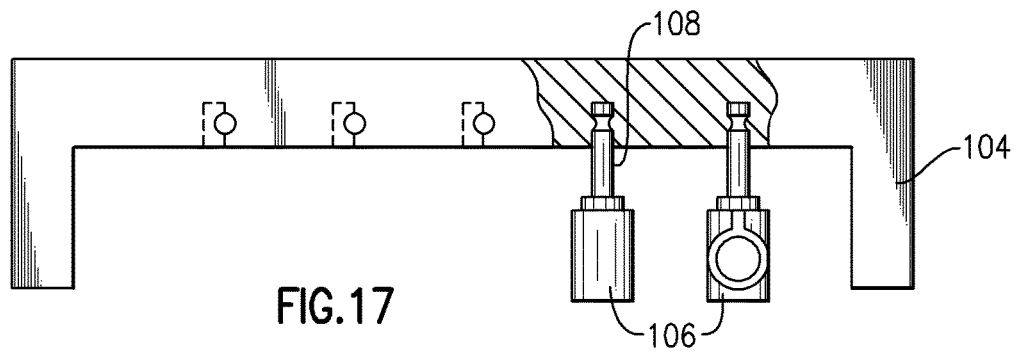
FIG. 17 is a fragmentary perspective view of sub-blanks mounted in a framework in accordance with an embodiment of the present invention.
Figure 18:
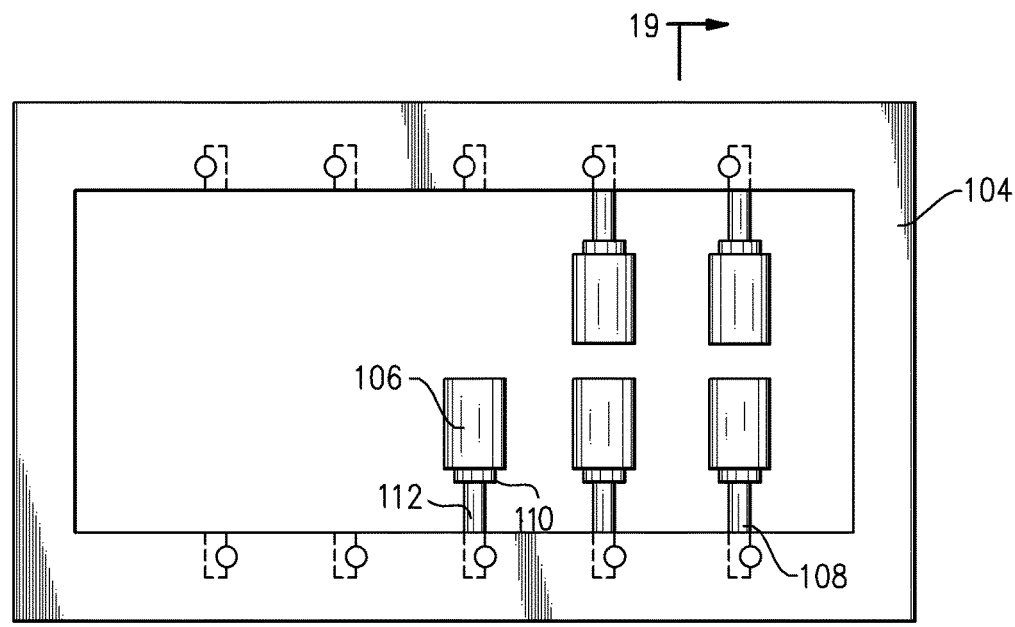
FIG. 18 is a fragmentary perspective view of sub-blanks mounted in a framework in accordance with an embodiment of the present invention.
Figure 19:
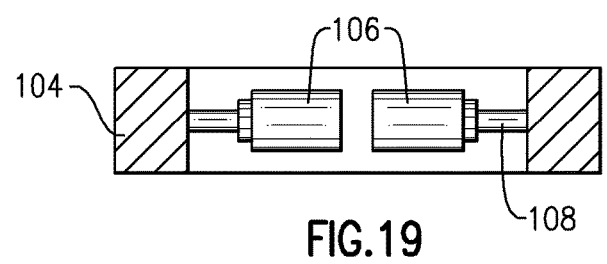
FIG. 19 is a cross-sectional view of sub-blanks mounted in a framework taken at line 19-19 of FIG. 18.
Figure 20:
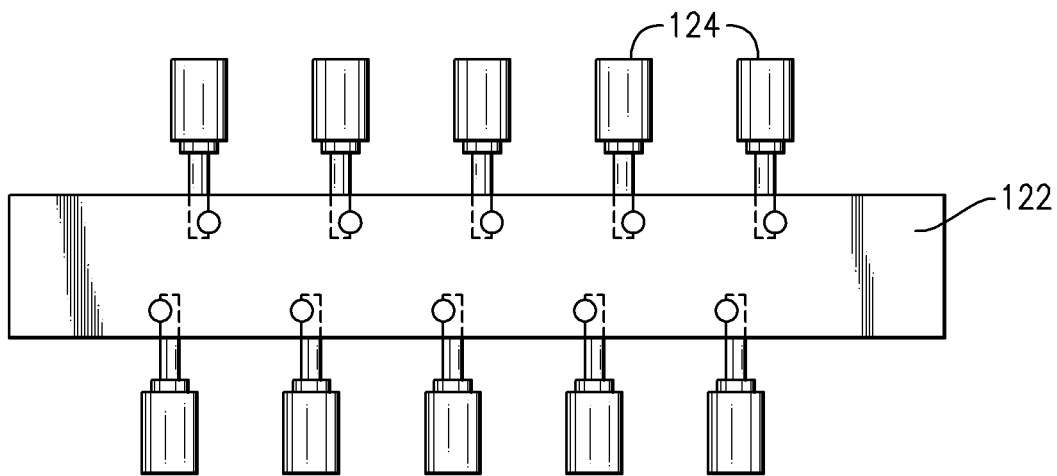
FIG. 20 is top perspective view of sub-blanks mounted onto a framework in accordance with an embodiment of the present invention.
Figure 21:
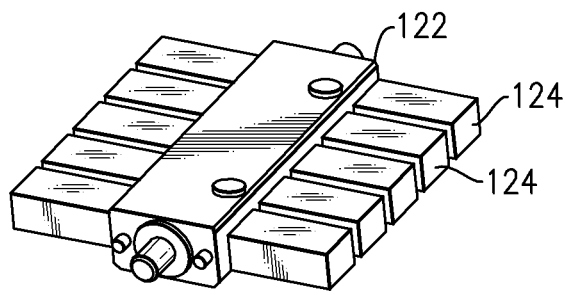
FIG. 21 is side top perspective view of sub-blanks mounted onto a framework in accordance with an embodiment of the present invention.
Figure 22:
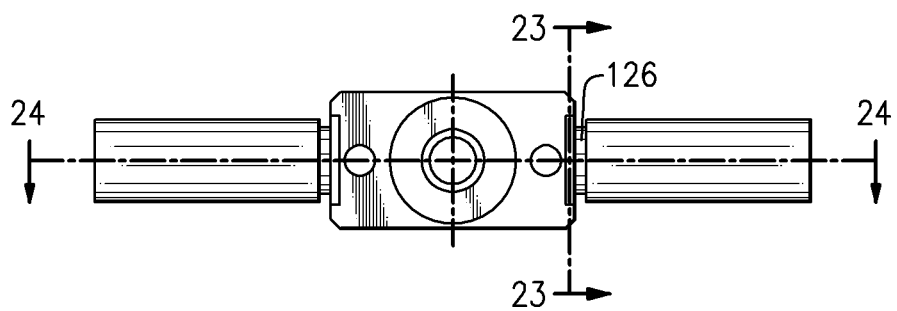
FIG. 22 is a side view of the framework in FIG. 21.

FIGS. 17 through 19 show a rectangular-shaped framework 104 having sub-blanks 106 aligned in two rows, attached at opposite sides of framework 104. Sub-blanks 106 are shown attached to a support 108, which is attached to framework 104. Support 108 includes a flange 110 and a shaft 112 for attachment to framework 104. FIG. 19 is a cross-sectional view of FIG. 18 at line 19-19 of FIG. 18.

Figure 23:
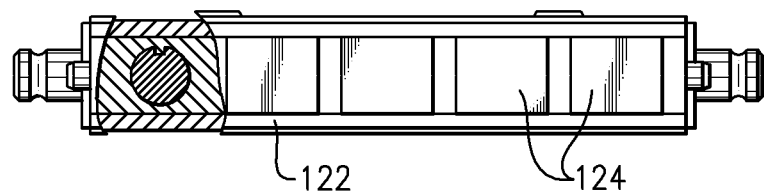
FIG. 23 is front plan view of the framework of FIG. 21, with a partial cross-sectional view at line 23-23 of FIG. 22.
Figure 24:
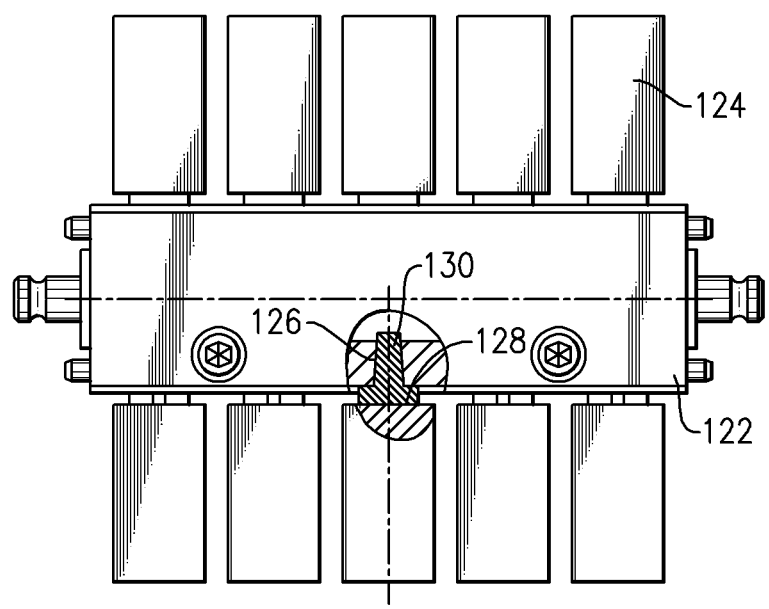
FIG. 24 is top perspective view of the framework of FIG. 21, with a partial cross-sectional view at line 24-24 of FIG. 22.

FIGS. 20 through 24 show yet another embodiment of a cluster blank 120 having a rectangular-shaped framework 122 with a series of sub-blanks 124 attached along both sides of framework 122. Sub-blanks 124 are attached to a support 126, which fits into framework 122. Support 126 includes a flange section 128 and a shaft 130, which extends into framework 122. In this example, the portion of the sub-blank to be milled is disposed completely outside the framework. FIG. 23 is a partial cross-sectional view at line 23-23 of FIG. 22. FIG. 24 is a top perspective view of the framework of FIG. 21, with a partial cross-sectional view at line 24-24 of FIG. 22.

Figure 25:
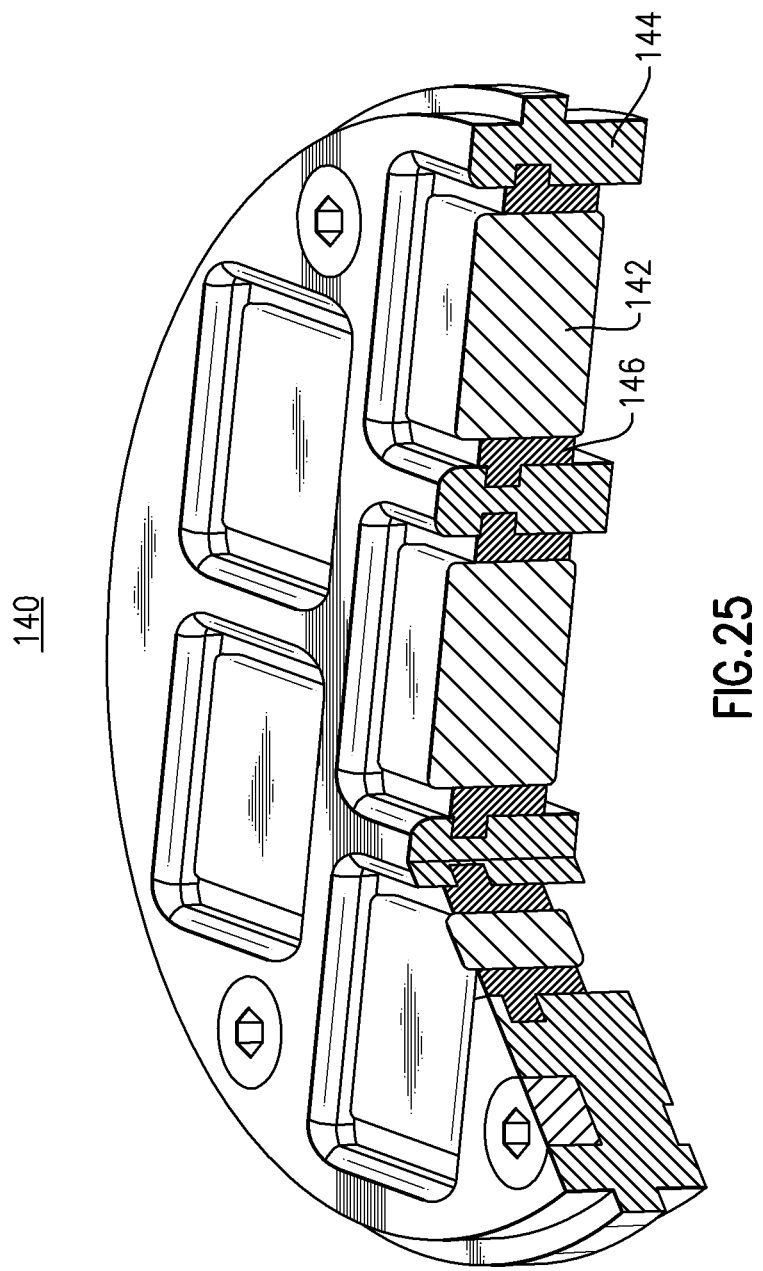
FIG. 25 is a fragmentary perspective view of a cluster blank in accordance with an embodiment of the present invention.
Figure 26:
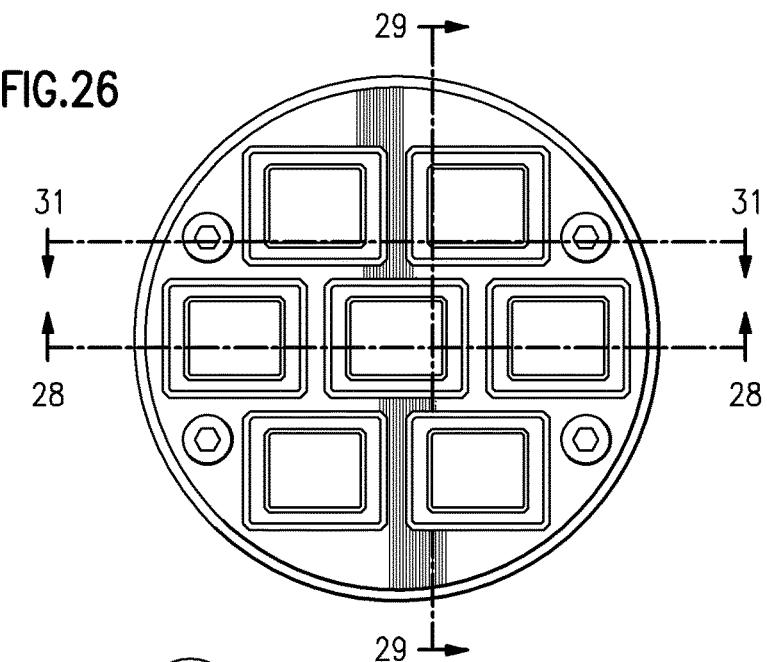
FIG. 26 is a top plan view of a cluster blank in accordance with an embodiment of the present invention.
Figure 27:
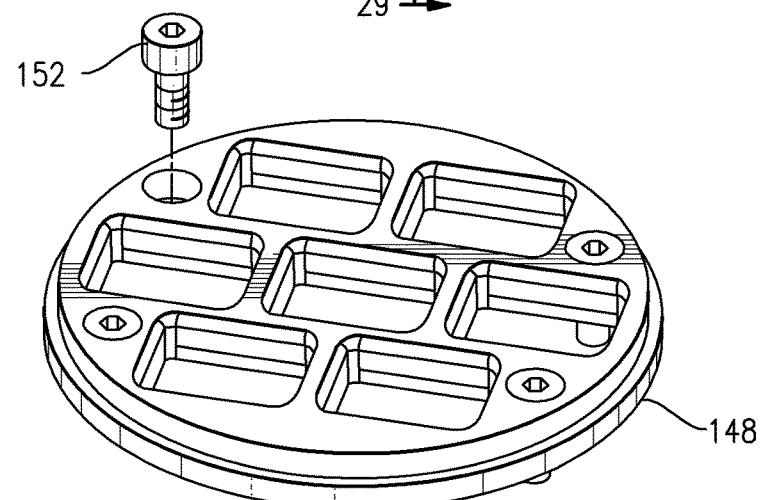
FIG. 27 is an exploded view of the cluster blank assembly of FIG. 26.
Figure 27:
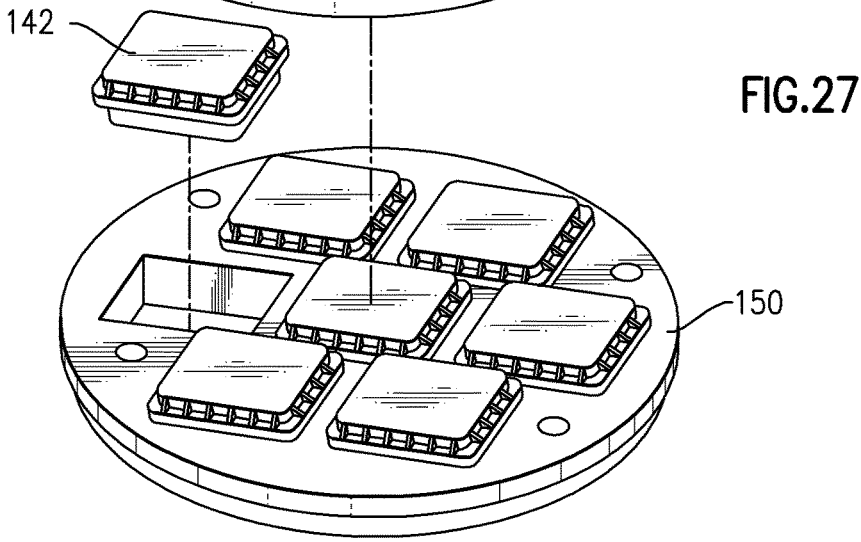

FIGS. 25 through 27 illustrate a cluster blank 140 having sub-blanks 142 inserted and attached to a round framework 144. The cut-away view in FIG. 25 illustrates the sub-blank in position and attached or fitted snugly into a receptacle 146 which fits into framework 144.

FIG. 27 illustrates an exploded view of cluster blank 140 showing a top section 148 and a bottom section 150 of framework 144. Sub-blanks 142 are placed in bottom section 150 and top section 148 is positioned over sub-blanks 142 and bottom section 150 to hold sub-blanks 142 in place during milling. A bolt 152 or similar fastening means is inserted into a series of openings in the top and bottom sections to fasten and hold the sections together.

Figure 28:
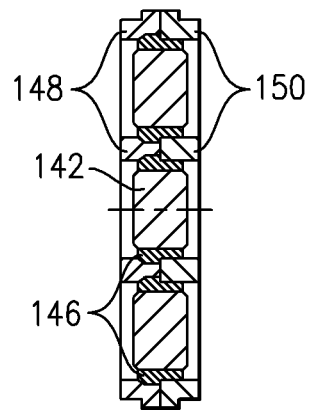
FIG. 28 is a cross-sectional view of the cluster blank of FIG. 26 taken at line 28-28 of FIG. 26.
Figure 29:
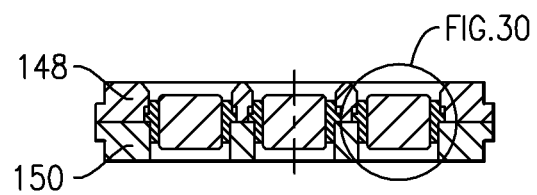
FIG. 29 is a cross-sectional view of the cluster blank of FIG. 26 taken at line 29-29 of FIG. 26.
Figure 30:
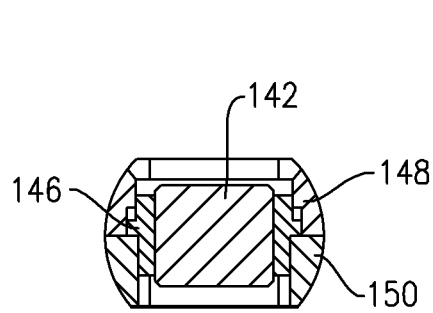
FIG. 30 is an enlarged view of a sub-blank fitting in FIG. 29.
Figure 31:
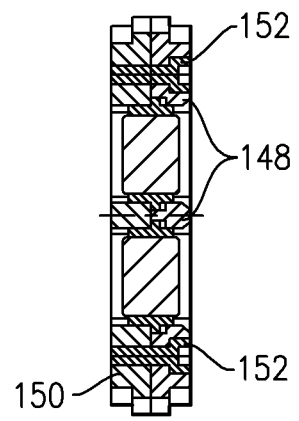
FIG. 31 is a cross-sectional view of the cluster blank of FIG. 26 taken at line 31-31 of FIG. 26.
Figure 33:
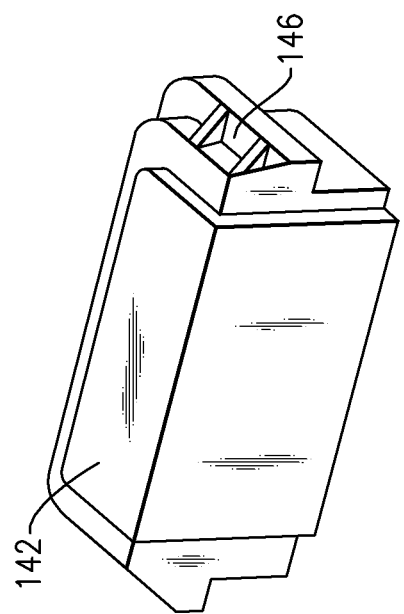
FIG. 33 is a fragmented view of the sub-blank of FIG. 32.
Figure 32:
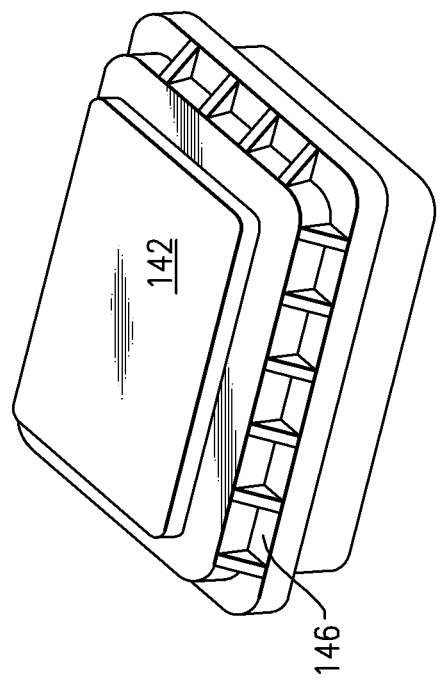
FIG. 32 is a perspective view of a sub-blank in a receptacle in accordance with the present invention.

FIGS. 28 through 33 show cross-sectional views of sub-blanks 142 positioned in framework 144. FIG. 28 is a cross-sectional view of the cluster blank of FIG. 26 taken at line 28-28 of FIG. 26. FIG. 29 is a cross-sectional view of the cluster blank of FIG. 26 taken at line 29-29 of FIG. 26. FIG. 30 is an enlarged view of a sub-blank fitting in FIG. 29. Each sub-blank is shown attached to holder 146 which is positioned on bottom section 150. Top section 148 is fitted onto bottom section 150 and bolts 152 or similar means hold top and bottom sections together. As clearly shown in FIG. 30, the sharp edge of the holder 146 squeezes into the framework unit 148. FIG. 31 is a cross-sectional view of the cluster blank of FIG. 26 taken at line 31-31 of FIG. 26. FIGS. 32 and 33 more clearly show the sharp edge of holder 146 that fits within framework 148. Sub-blanks 142 may be glued or similarly attached to 146 or the latter can snugly contain the sub-blanks and serve as compression fittings, i.e., being squeezed by top and/or bottom sections. It should be mentioned that the layout of the sub-blanks in framework 148 may be any configuration including those shown in FIGS. 3 through 7 and 9 through 11. Holder 146 may be fabricated of a flexible, elastic or rubber material. Moreover, the holder may be fitted to the cluster blank by a snap connection or a compression fit. In all embodiments, the sub-blanks may be attached directly to the framework, or attached to an intermediate piece, which is attached to the framework.

The following example illustrates the increased yield, and reduced material waste, that can result from replacing a one-piece disk or blank with a cluster blank formed according to the present invention.

Individual ZirCAD blocks of two sizes—C14 and B40 (from e.max CAD) are used as sub-blanks. A Charly4dental CNC milling machine 56 (see, e.g., FIG. 8) for serial production of dental prostheses (available from Charlyrobot, Cruseilless, France) is used. Charly4dental is equipped with a disk fixing system capable of housing two 100 mm (~4") or smaller disks 58. It is primarily designed for dry-milling of soft-sintered zirconia and resin disks (like PMMA). A first 100 mm PMMA disk is used to fabricate the framework (template) for a cluster blank using the same milling machine. Four symmetrically arranged rectangular openings with the dimensions of 25×20 mm$^2$ and 45×20 mm$^2$ are milled in PMMA disk, then 2 ZirCAD C15, and 2 of C40 zirconia blanks are placed in the openings and the resulting even gaps filled with LECOSET 100 castable mounting material (available from LECO, product#812-125). Two 3-unit bridges and 2 molars are milled into the sub-blanks. If a one-piece 100 mm zirconia disk is used, the remaining zirconia will have to be disposed of, as shown in FIG. 2. In case of a cluster blank, the remnants of sub-blanks are removed and PPMA framework can be reused to assemble the next cluster blank.

All numbers expressing quantities or parameters used in the specification are to be understood as additionally being modified in all instances by the term "about". Notwithstanding that the numerical ranges and parameters set forth, the broad scope of the subject matter presented herein are approximations, the numerical values set forth are indicated as precisely as possible. For example, any numerical value may inherently contains certain errors, evidenced by the standard deviation associated with their respective measurement techniques, or round-off errors and inaccuracies.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A CAD/CAM system for the fabrication of dental articles comprising:
   one or more milling machines;
   one or more blank holders in the one or more milling machines;
   a cluster milling blank comprising a framework constructed to cooperate with the one or more blank holders;
   a plurality of sub-blanks attached to the framework, wherein the sub-blanks are optimally arranged in an addressable matrix designed from nesting software;
   wherein the nesting software has at least a second order level of functionality, wherein the second order level of functionality comprises a statistical function, wherein the statistical function provides statistics on size and shape distribution for milling envelopes based on parameters received from a history of prior milling operations or prior business operations;
   wherein the parameters comprise at least one of type of dental case, dental material selection, size of dental articles, shape of dental articles, shade of dental articles, optimal tool path, and milling parameters; and
   wherein a portion of the sub-blanks are to be milled into dental articles.

2. The CAD/CAM system of claim 1 wherein the dental articles comprise a coping, pontic, framework, denture teeth, space maintainer, tooth replacement appliance, orthodontic retainer, denture, post, facet, splint, cylinder, pin, connector, crown, partial crown, veneer, onlay, inlay, bridge, fixed partial denture, implant or abutment.

3. The CAD/CAM system of claim 1 wherein the nesting software optimizes the number, type, size, shade, and arrangement of sub-blanks that can fit into the framework to accomplish mill jobs waiting to be completed in a job queue.

4. The CAD/CAM system of claim 1 wherein the nesting software estimates size and shape of milling envelopes corresponding to mill jobs in a job queue based on prior statistics or case electronic data; computes the required number of sub-blanks and frameworks; orders assembly of the sub-blanks and frameworks into the required number of cluster blanks; and optimally distributes mill jobs between the sub-blanks and the cluster blanks to minimize material waste and shade inventory.

5. The CAD/CAM system of claim 1 wherein the nesting software collects data on prior milling envelopes to determine the maximum length (MEL) and maximum width (MEW) of the milling envelopes for single unit, three-unit, four-unit or larger-number-unit dental articles and correlates size and shape with number of units and type of dental article.

6. The CAD/CAM system of claim 1 wherein the nesting software order of functionality is based on an N/n ratio wherein N is a characteristic batch size corresponding to a number of cases that the software handles simultaneously and n is the average number of units that are milled in a cluster blank.

7. The CAD/CAM system of claim 6 wherein n is at least 7 or greater.

8. The CAD/CAM system of claim 6 wherein n is at least 10 or greater.

9. The CAD/CAM system of claim 6 wherein n is at least 30 or greater.

10. The CAD/CAM system of claim 6 wherein the nesting software has at least a second order level of functionality and the N/n ratio is between 10 and 100.

11. The CAD/CAM system of claim 6 wherein the nesting software has at least a third order level of functionality and the N/n ratio is greater than 100.

12. The CAD/CAM system of claim 10 wherein N is a batch number equal to at least one hundred cases a business day for one milling machine.

13. The CAD/CAM system of claim 10 wherein N is a batch number equal to much larger than one hundred cases a business day for one milling machine but is not greater than 500 cases comprising cases at different stages of processing, for an entire milling center having more than two high productivity milling machines.

14. The CAD/CAM system of claim 11 wherein N is a batch number equal to at least seven hundred cases a business day comprising cases at different stages of processing for an entire milling center comprising more than two high productivity milling machines.

15. The CAD/CAM system of claim 11 wherein N is a batch number equal to greater than seven hundred cases a business day comprising cases at different stages of processing for an entire milling center comprising more than two high productivity milling machines.

16. The CAD/CAM system of claim 1 wherein the framework is in the shape of a disc with a series of sub-blanks disposed in the disc.

17. The CAD/CAM system of claim 1 wherein the sub-blanks are attached to the framework and wherein the portion of the sub-blank to be milled is disposed completely outside of the framework.

18. The CAD/CAM system of claim 1 wherein the framework comprises a plurality of openings for receiving sub-blanks; wherein the framework comprises an upper segment and a lower segment; and a plurality of receptacles located in the plurality of openings for retaining the plurality of sub-blanks in the framework.

19. The CAD/CAM system of claim 18 wherein the upper segment maintains the receptacles in position in the framework.

20. The CAD/CAM system of claim 1 wherein the second order level of functionality further comprises an N/n ratio of 10 to 100, where N comprises the number of cases optimized concurrently and n comprises the average number of individual units per blank;
a characteristic batch size between 70 and 700;
a single blank optimization function;
a placement function;
a sub-blank optimization function, and
a planning function.

21. The CAD/CAM system of claim 1 further comprising a third order level of functionality, wherein the third order level of functionality comprises a virtual statistics function, wherein the virtual statistics function uses CAD files for future mill jobs to forecast size and shape distribution for milling envelopes.

22. The CAD/CAM system of claim 21 wherein the third order level of functionality further comprises an N/n ratio of 10 to 100, where N comprises the number of cases optimized concurrently and n comprises the average number of individual units per blank;
a characteristic batch size between 70 and 700;
a single blank optimization function;
a placement function;
a statistical function;
a sub-blank optimization function,
a planning function;
a cluster blank template optimization function; and
a robotic function.

23. A method of milling dental articles using a CAD/CAM system comprising:

statistically analyzing data corresponding to milled dental objects with nesting software thereby obtaining a size and shape distribution for milling envelopes and their correlation with specific types of dental articles, wherein the data analyzed is based on parameters comprising at least one of type of dental case, dental material selection, size of dental articles, shape of dental articles, shade of dental articles, optimal tool path, and milling parameters;
selecting a batch of dental cases corresponding to objects to be milled by selecting their corresponding electronic data;
optimizing, by the nesting software, an addressable matrix arrangement of a plurality of sub-blanks selected for milling the batch of dental cases;
assembling the selected sub-blanks on to one or more frameworks utilizing one or more templates to produce one or more cluster blanks;
and
milling the sub-blanks into dental articles.

24. The method of claim 23 wherein the dental articles comprise a coping, pontic, framework, denture teeth, space maintainer, tooth replacement appliance, orthodontic retainer, denture, post, facet, splint, cylinder, pin, connector, crown, partial crown, veneer, onlay, inlay, bridge, fixed partial denture, implant or abutment.

25. The method of claim 23 further comprising: reacquiring actual or virtual statistics from the milling step, and modifying or redesigning the one or more templates based on maximum average yield, minimum waste per sub-blank and minimum sub-blank shade inventory criteria.

26. The method of claim 25 further comprising: milling the modified or redesigned templates from precursor blanks using the CAD/CAM system.

* * * * *